United States Patent [19]
Vigil

[11] Patent Number: 5,209,799
[45] Date of Patent: May 11, 1993

[54] METHOD FOR MANUFACTURING A FOLDING BALLOON CATHETER

[75] Inventor: Dennis Vigil, San Diego, Calif.

[73] Assignee: InverVentional Technologies, Inc., San Diego, Calif.

[21] Appl. No.: 870,149

[22] Filed: Apr. 17, 1992

[51] Int. Cl.⁵ .................... B32B 3/26; A61M 25/10
[52] U.S. Cl. .................... 156/156; 156/221; 604/271; 606/170
[58] Field of Search ............ 156/156, 165, 198, 221; 606/159, 170, 191, 192, 198; 604/53, 96, 103, 264, 267

[56] References Cited

U.S. PATENT DOCUMENTS

| | | | |
|---|---|---|---|
| 4,263,236 | 4/1981 | Briggs et al. | 156/294 |
| 4,273,128 | 6/1981 | Lary | 606/159 |
| 5,015,231 | 5/1991 | Keith et al. | 604/103 |
| 5,100,425 | 3/1992 | Fischell et al. | 606/159 |
| 5,147,302 | 9/1992 | Euteneuer et al. | 606/191 |

FOREIGN PATENT DOCUMENTS 3400416  7/1985  Fed. Rep. of Germany ...... 606/191

*Primary Examiner*—Michael W. Ball
*Assistant Examiner*—Robert W. Robey
*Attorney, Agent, or Firm*—Nydegger & Associates

[57] ABSTRACT

A method of manufacturing a folding balloon catheter for use as an angioplasty device, wherein the balloon catheter has atherotomes attached to the exterior of the balloon, includes inflating a balloon to its expanded state. A plurality of patches of a curable elastomer adhesive are then applied at selected locations on the outside surface of the inflated balloon, and an atherotome is attached to the balloon at each of the patches. The inflated balloon, with attached atherotomes, is then partially cured to more firmly attach the atherotomes to the balloon. The balloon is then deflated to a contracted configuration in a manner which forms a plurality of flaps in the balloon between the atherotomes. The deflated balloon is then cured to completion to establish a permanent set in the flaps which enable the balloon catheter to be repeatedly inflated and deflated during operation between predictable expanded and contracted configurations.

18 Claims, 1 Drawing Sheet

METHOD FOR MANUFACTURING A FOLDING BALLOON CATHETER

FIELD OF THE INVENTION

The present invention relates generally to a method of manufacturing devices which dilate blood vessels across a stenotic segment of the vessel. In particular, the present invention relates to a method of manufacturing angioplasty devices. The present invention more particularly, though not exclusively, relates to a method for manufacturing an angioplasty device which employs a folding balloon catheter having atherotomes mounted along the outer surface of the balloon.

BACKGROUND OF THE INVENTION

Blockage of human arteries is a widespread malady and, as such, represents a significant health concern. Blockages reducing blood flow through the coronary arteries to the heart can cause heart attacks, while blockages reducing blood flow through the arteries to the brain can cause strokes. Similarly, arterial blockages reducing blood flow through arteries to other parts of the body can produce grave consequences in an affected organ or limb.

The build-up of atherosclerotic plaque is a chief cause of blockages, termed stenoses, which reduce blood flow through the arteries. Consequently, several methods have been introduced to alleviate the effects of plaque build-up restricting the artery. One such method is a procedure termed angioplasty, which uses an inflatable device positioned at the stenosis to dilate the artery. A typical angioplasty device is disclosed in U.S. Pat. No. 4,896,669 to Bhate et al. The angioplasty device of Bhate et al includes an inflatable balloon which is attached to the distal end of a hollow catheter tube. The proximal end of the catheter tube is attached to a fluid source.

To treat an arterial stenosis, the balloon of Bhate et al is introduced into the artery in a deflated state and guided through the artery over a guide wire to a position adjacent the stenosis. Fluid from the fluid source is then infused into the balloon via the catheter tube to inflate the balloon. As the balloon expands, it presses against the arterial wall in the region of the stenosis, dilating the artery at the stenosis and restoring it to a sufficient size for adequate blood flow therethrough. The balloon is then deflated and removed from the artery, thereby completing the treatment.

A desirable feature of a balloon catheter is that the balloon be able to assume a neatly folded and compact configuration when it is in the deflated state. This is so in order to facilitate the insertion and passage of the balloon catheter through the blood vessel. Passage of the balloon through the vessel becomes even more difficult to accomplish if the structure of the balloon catheter is relatively complicated. Specifically, it has been proposed that a cutting element be used in concert with the operation of the balloon to facilitate dilation of the vessel at the stenosis As can be easily appreciated, safety also becomes an issue of concern when cutting elements are included. Even more so when these cutting elements are mounted directly onto the outer surface of the balloon.

In light of the above, it is an object of the present invention to provide a method for manufacturing a folding balloon catheter having a balloon with a predictable folded configuration when the balloon is deflated. It is another object of the present invention to provide a method for manufacturing a folding balloon catheter having atherotomes mounted on the outer surface of the balloon. It is yet another object of the present invention to provide a method for manufacturing a folding balloon catheter having atherotomes mounted on the balloon which is relatively easy to perform and comparatively cost effective.

SUMMARY OF THE INVENTION

The present invention is a method for manufacturing a balloon catheter which includes a plurality of elongated atherotomes that are attached to the outer surface of the balloon along predetermined crease lines. The device, as manufactured, is useful in an angioplasty procedure to incise stenotic tissue in a blood vessel, and to thereby facilitate dilation of the vessel as the balloon is expanded.

In accordance with the present invention, the method for manufacturing a balloon catheter is initiated by positioning a substantially cylindrical shaped balloon membrane over a portion of a hollow catheter tube. More specifically, the ends of the balloon membrane are inwardly tapered and the portion of the catheter tube over which the balloon membrane is positioned, is formed with a fluid port. The fluid port is thus located intermediate the ends of the balloon membrane and the ends are then fixedly attached to the catheter tube. This creates a fluid chamber between the catheter tube and the wall of the balloon membrane and fluid communication is established between this chamber and the catheter tube through the fluid port. Accordingly, fluid flow into and out of the chamber through the fluid port will respectively inflate and deflate the balloon.

With the balloon inflated, a thin layer of a curable elastomer adhesive, such as urethane, is applied at selected locations on the outside of the balloon wall. This creates adhesive patches on the surface of the balloon where the atherotomes are to be attached. As contemplated by the present invention, each atherotome is an elongated structure that includes a blade with a cutting edge. The blade itself is embedded in an elastomer base that will adhere to the patch of elastomer adhesive on the balloon. As further contemplated by the present invention, when the atherotome is attached to the balloon, the cutting edge of the atherotome faces radially outward from the axis of the balloon catheter. Consequently, each atherotome is oriented substantially parallel to the catheter tube and each atherotome extends for a substantial distance along the length of the balloon.

Once the atherotomes have been attached to the balloon as desired, the balloon is heated to a predetermined partial curing temperature and maintained at that temperature for a predetermined period of time. This partial curing accomplishes an important purpose. After partial curing, the adhesive patches are no longer tacky to the touch and the atherotomes are more securely attached to the balloon.

When partial curing has been completed, the balloon is deflated. Not unexpectedly, as the balloon is deflated, furrows and folds or flaps form in the balloon wall. For the present invention it is important that the location of the furrows and flaps in the balloon be predictable. Specifically, the furrows need to be along those portions of the balloon where the atherotomes are attached.

The preferred orientation of the furrows, and thus the flaps between the furrows, is facilitated by using a special folding tool. This tool comprises a body having a central cylindrical aperture. Additionally, the tool has a plurality of linear slots which extend radially from the central aperture. Slidably positioned within each of these slots is a planar member that is inwardly biased by a spring toward the aperture.

For the operation of the special tool, an inflated balloon with attached atherotomes is inserted into the aperture of the tool. This is done after the partial curing step. As so positioned, the cutting edge of each atherotome extends into a respective slot of the special tool and each of the planar members urges inwardly against the cutting edge of a respective atherotome. As the balloon is subsequently deflated, the planar members are moved inwardly to displace the atherotomes toward the center of the aperture This displacement establishes a folded configuration for the balloon. In this folded configuration, the balloon is furrowed at the locations of the atherotomes, and those portions of the balloon membrane between the furrows are folded outwardly to create flaps of balloon membrane material between the atherotomes.

While in the folded configuration, the balloon is heated to a predetermined final curing temperature and is maintained at that temperature for a predetermined final curing time. This step cures all of the balloon membrane and creates a permanent set or memory in the membrane which will cause the balloon to return to its folded configuration whenever the balloon is deflated The novel features of this invention, as well as the invention itself, both as to its structure and its operation will be best understood from the accompanying drawings, taken in conjunction with the accompanying description, in which similar reference characters refer to similar parts, and in which:

DESCRIPTION OF PREFERRED EMBODIMENTS

Figure 1:
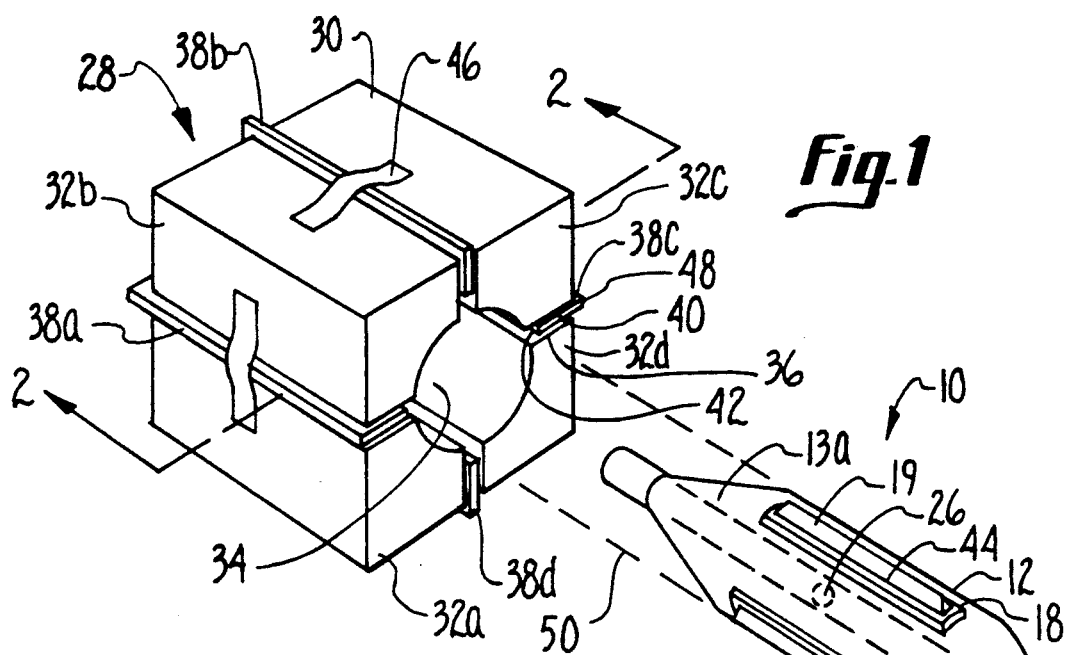
FIG. 1 is a perspective view of a balloon catheter in a separated relationship with a folding tool used in the manufacturing method of the present invention.

The present invention is a multi-step method of manufacturing a folding balloon catheter, such as the balloon catheter shown in FIG. 1 and generally designated 10. In accordance with the present invention, the method for manufacture is initiated by joining a conventional angioplasty balloon 12 with a hollow catheter tube 14. The balloon 12 is preferably shaped as a hollow tubular structure having a thin outer wall 16. As seen in FIG. 1, the ends 13a and 13b of balloon 12 are tapered inwardly. Preferably, the wall 16 of balloon 12 is made of a pliant polymeric material which encloses and defines an interior chamber 17 which is, perhaps, best seen in FIG. 2A. Preferably balloon 12 is made of a material well known in the art, such as a biaxially oriented material. The catheter tube 14 is flexible and, like balloon 12, is preferably formed from a polymeric material. Additionally, catheter tube 14 has a port 26 that is positioned near one end of the tube 14.

In order to join the balloon 12 to catheter tube 14, the tube 14 is inserted into balloon 12 to extend through the chamber 17. Thus, port 26 is positioned within the chamber 17 The ends 13a and 13b of balloon 12 are then sealed to catheter tube 14. Consequently, any fluid communication with the chamber 17 can only be accomplished from catheter tube 14 through the port 26. The seal between ends 13a and 13b of balloon 12 and catheter tube 14 is effected by any known bonding technique such as adhesive bonding or thermal bonding. The result is a balloon catheter structure which is further modified according to the steps described hereafter.

With the balloon 12 attached to catheter tube 14, the balloon 12 is inflated. This is done by infusing a fluid such as air into the balloon chamber 17, under pressure, which causes the balloon chamber 17 to expand. When balloon 12 is inflated, wall 16 defines a substantially cylindrical surface having tapered ends. A thin layer of an elastomeric adhesive (preferably urethane) is then applied to the exterior surface of the balloon wall 16 at preselected points to form adhesive patches 18. These patches 18 are preferably elongated and rectangular in shape. Further, the patches 18 are preferably aligned to be parallel with the longitudinal axis of the balloon 12 and equidistantly spaced from adjacent patches 18 about the periphery of the balloon. The adhesive for creating the patches 18 is preferably a curable resin such as a polyurethane which is applied in a liquid or semi-liquid state by means such as dipping, spraying or painting.

When initially applied onto the surface of wall 16 of balloon 12, the adhesive patches 18 are tacky. This makes it possible to mount an atherotome 19 onto each of the patches 18 as desired. In a preferred embodiment of the present invention, at least three atherotomes 19 are mounted onto the balloon 12. The actual number of atherotomes 19 will, obviously, correspond to the number of patches 18 on balloon 12, since each atherotome 19 is mounted on a single adhesive patch 18. In order to make the attachment, each atherotome 19 is firmly embedded into a polyurethane base 21 which dimensionally corresponds in shape to the patch 18. Preferably, however, the patch 18 is dimensioned somewhat larger than the base 21. With the bases 21 of atherotomes 19 stuck onto the outer surface of balloon 12, the balloon catheter 10 is now in set for a partial curing.

Partial curing is performed by placing the balloon 12 portion of balloon catheter 10 in an oven (not shown) that has been preheated to a predetermined partial curing temperature. Preferably, partial curing temperature is in the range of between about one hundred and twenty and one hundred and seventy degrees Fahrenheit (120°-170° F.), and more preferably at a partial curing temperature of about one hundred and sixty degrees Fahrenheit (160° F.). The balloon catheter 10 is maintained in the oven at the partial curing temperature for a predetermined partial curing time of between about fifteen and forty five minutes and, preferably, for a partial curing time of about one half hour. As a consequence of partial curing, the adhesive patches 18 lose their tackiness, and the atherotomes become fixedly attached to balloon 12.

The balloon catheter 10 is now in a condition for the additional processing that is necessary to insure the balloon 12 will predictably assume a desired configuration when deflated. FIG. 1 shows balloon catheter 10 in position for the deflation and folding steps that follow the partial curing step. Specifically, balloon 12 is shown inflated to its expanded condition with atherotomes 19 mounted on adhesive patches 18.

As intended for the present invention, the deflation and folding steps in the method of manufacture are performed simultaneously by means of a special folding tool, shown in FIG. 1 and generally designated 28. As shown, tool 28 has a body 30 that is segmented into four identical sections 32 a–d which are positioned to surround and define a central aperture 34. As so positioned, sections 32 a–d establish the slots 36 a–d which separate adjacent sections 32 from each other. It is to be appreciated that tool 28 shown in FIG. 1 is only exemplary. The number of sections 32 which are used to create body 30 will vary depending on the number of atherotomes 19 to be mounted on balloon 12.

As also shown in FIG. 1, a planar member 38 is slidably positioned within each slot 36. Each of the planar members 38 is a substantially identical stiff metal panel having a pad 40 which is affixed to, and coextensive with, the axial edge 42 of member 39. Pad 40 is formed from a relatively resilient material, such as an elastomer or a plastic, to cushion its contact with the sharpened cutting edge 44 of each atherotome 19.

Aperture 34, slots 36 a–d and planar members 38 a–d are dimensioned such that when balloon 12 is in an expanded condition, balloon 12 fits snugly within aperture 34. As balloon 12 is inserted into aperture 34, each slot 36 receives one of the cutting edges 44 of atherotome 19. When initially inserted into the slots 36 the cutting edges 44 of atherotomes 19 do not abut with pad 40 of a planar member 38.

Attached to the body 30 of tool 28 and associated with slot 36 a–d is some means for respectively urging each planar member 38 inwardly toward the central aperture 34. In one embodiment of the present invention, this urging means is a band spring 46 which is attached to the outside of body 30 substantially perpendicular to slot 36. Each spring 46 is positioned across one of the slots 36 a–d to abut the outside edge 48 of the planar member 38 in the particular slot 36.

For the loading configuration of tool 28, as shown in FIGS. 1 and 2, springs 46 are deformed to bias members 38 inwardly toward the central aperture 34. Means (not shown) may be further provided for withdrawing planar members 38 away from the central aperture 34 and for maintaining planar members 38 in this loading position.

Figure 2A:
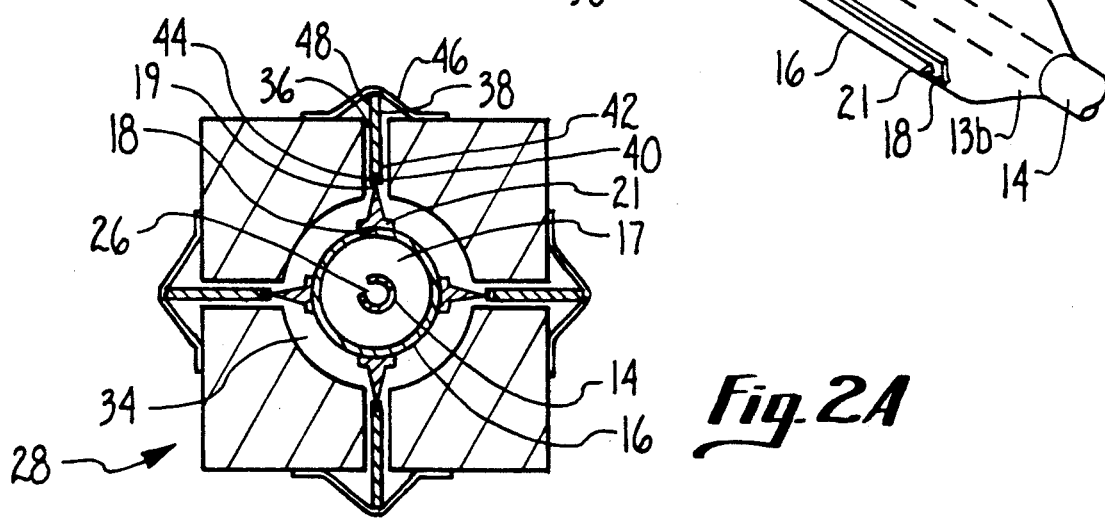
FIG. 2A is a cross-sectional view of an expanded balloon catheter inserted into the folding tool as seen along line 2—2 in FIG. 1 prior to the deflation step in the manufacturing method of the present invention.

As indicated above, the deflation and folding steps are performed by first inserting an inflated balloon 12 into the central aperture 34 of tool 28 along the path of dotted lines 50 shown in FIG. 1. Referring now to FIG. 2A, balloon 12 and catheter tube 14 are shown to be coaxially positioned in the aperture 34 of tool 28. Once balloon 12 is so positioned, planar members 38 are biased by springs 46 toward central aperture 34. This causes the pads 40 of planar members 38 a–d to abut cutting edges 44 of atherotomes 19. At this point in the process, the fluid pressure inside interior chamber 17 of balloon 12 prevents the biased planar members 38 from collapsing balloon 12.

Figure 2B:
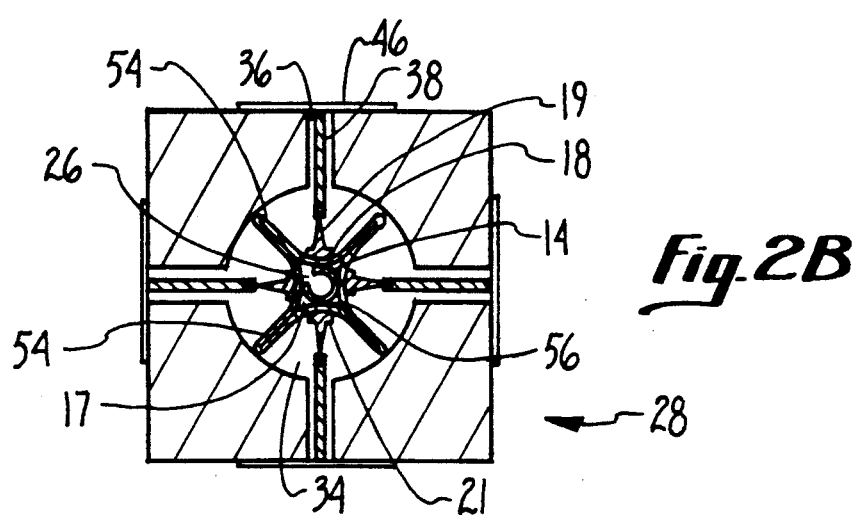
FIG. 2B is a cross-sectional view of the balloon catheter in its contracted state as would be seen in FIG. 2A after performing the deflation step in the manufacturing method of the present invention.

Balloon 12 is now collapsed. To do this, the fluid in interior chamber 17 is withdrawn at a controlled rate through port 26 and catheter tube 14. As shown in FIG. 2B, the result is that springs 46 urge planar members 38 toward central aperture 34 to reconfigure the collapsing balloon 12.

As indicated above, during reconfiguration of the collapsing balloon 12, planar members 38 drive against the atherotomes 19. Simultaneously, the wall 16 of balloon 12 is folded to create flaps 54 which are formed between the atherotomes 19. Additionally, furrows 56 are set into the balloon wall 16 at the location of each adhesive patch 18 and corresponding atherotome 14. During this step, flaps are established substantially parallel to each other and are aligned with the longitudinal axis of the balloon catheter 10. The deflation and folding steps are, thus, completed and the balloon 12 is removed from the central aperture 34 of tool 28 in a folded or contracted configuration.

The last step of the present method is the final curing of the balloon 12. Final curing is performed by placing balloon 12 in an oven (not shown) that has been preheated to a predetermined final curing temperature in a range of between about one hundred and twenty and one hundred and seventy degrees Fahrenheit (120°–170° F.), and more preferably at a partial curing temperature of about one hundred and sixty degrees Fahrenheit (160° F.). The balloon 12 is maintained in the oven at this final curing temperature for a predetermined final curing time of between eight and twelve hours (8–12 hrs). Preferably, this final curing time is of about 8 hours. Thus, it is apparent that the final curing step is distinguishable from the partial curing step in the present case by the length of the curing time, i.e., the final curing time is considerably longer than the partial curing time although the curing temperatures may be the same.

The balloon catheter is now in a suitable condition for its intended use. During the manufacturing steps set forth above, it has happened that the flaps 54 and creases 56 in balloon 12 which are formed during the previously described folding step are rendered permanent by the final curing step. Thus, for subsequent inflations and deflations of balloon 12 the preset flaps 54 and creases 56 enable substantially identical replication of the balloon's configurations when alternating between the expanded and contracted states.

After the balloon catheter 10 of the present invention has been assembled, it can be neatly packaged by performing the following generalized steps. First, after the final cure has been completed, balloon 12 of balloon catheter 10 is inserted into a silicone rubber tube (not shown) while the balloon 12 is still in a deflated configuration. The silicone rubber tube needs to have an inner diameter which is approximately equal to the outer diameter of the collapsed balloon 12 so that the collapsed balloon 12 can fit snugly inside the lumen of the silicone rubber tube. Further, the silicone rubber tube must be sufficiently long so that its ends extend beyond both of the ends 13a and 13b of balloon 12. Next, fluid is infused into interior chamber 17 of the balloon 12 through catheter tube 14 to inflate the balloon 12 inside the silicone rubber tube.

At this point, inflation of the balloon 12 has also expanded the lumen of the silicone rubber tube. With balloon 12 still inside the silicone rubber tube, while the balloon 12 is initially inflated, the ends of silicone rubber tube are pulled apart to contract the lumen of the silicone rubber tube. This contraction of the lumen of the silicone rubber tube forces the balloon 12 to draw down into an extremely compact configuration. When balloon 12 is in the compact configuration, balloon catheter 10 can be easily packaged in a retainer tube for storage or shipping.

While the particular method of manufacturing a folding balloon catheter as herein shown and disclosed in detail is capable of obtaining the objects and providing the advantages hereinbefore stated, it is understood that this particular method of manufacturing is merely illustrative of presently preferred embodiments of the invention. It is further understood that the present invention is not intended to be so limited and that other embodiments are further possible within the scope of the present invention.

I claim:

1. A method of manufacturing a folding balloon catheter having an elongated balloon enclosing an expandable chamber and a hollow catheter tube attached to the balloon in fluid communication with the chamber, the method comprising the steps of:
   introducing fluid into said chamber to inflate said balloon;
   applying a plurality of patches of an elastomeric material to the exterior of said balloon; partially curing said inflated balloon by heating said balloon to a predetermined partial curing temperature and maintaining said partial curing temperature for a predetermined partial curing time;
   withdrawing fluid from said chamber to collapse said balloon at said patches to form rounded furrows thereat, so as to fold said balloon and create flaps between said patches; and
   curing said collapsed balloon by heating said material to a predetermined final curing temperature and maintaining said final curing temperature for a predetermined final curing time.

2. A method of manufacturing a folding balloon catheter as recited in claim 1 wherein said elastomeric material is a synthetic resin.

3. A method of manufacturing a folding balloon catheter as recited in claim 1 wherein said partial curing temperature is substantially equal to said final curing temperature.

4. A method of manufacturing a folding balloon catheter as recited in claim 3 wherein said partial curing temperature and said final curing temperature are approximately 160° F.

5. A method of manufacturing a folding balloon catheter as recited in claim 1 wherein said final curing time is substantially greater than said partial curing time.

6. A method of manufacturing a folding balloon catheter as recited in claim 5 wherein said partial curing time is approximately 30 minutes and said final curing time is approximately 8 hours.

7. A method of manufacturing a folding balloon catheter as recited in claim 1 further comprising the step of mounting an atherotome on each said patch to fixably connect said atherotome to said balloon.

8. A method of manufacturing a folding balloon catheter as recited in claim 7 wherein said atherotomes are elongated and are mounted on said balloon substantially parallel to the longitudinal axis of said balloon and wherein each atherotome has a cutting edge facing radially outward from the longitudinal axis of said balloon when said atherotome is mounted on said balloon.

9. A method of manufacturing a folding balloon catheter attaching an elongated inflatable balloon in fluid communication with a catheter tube comprising the steps of:
   applying a plurality of patches of a curable elastomeric material in an uncured state to the exterior of said balloon while said balloon is inflated;
   attaching to each said patch an elongated atherotome having a cutting edge to orient said cutting edge of each said atherotome for facing radially outward from the longitudinal axis of said balloon;
   partially curing said balloon by heating said balloon to a predetermined partial curing temperature and maintaining said partial curing temperature for a predetermined partial curing time;
   collapsing said chamber to form a plurality of flaps in said balloon between said atherotomes; and
   curing said balloon to completion by heating said balloon to a predetermined final curing temperature and maintaining said final curing temperature for a predetermined final curing time.

10. A method of manufacturing a folding balloon catheter as recited in claim 9 wherein said balloon is collapsed to a contracted state by displacing each said atherotome toward the central longitudinal axis of said balloon using a collapsing means opposingly abutting said cutting edge of said atherotome.

11. A method of manufacturing a folding balloon catheter as recited in claim 10 further comprising the step of positioning said balloon in said collapsing means, said collapsing means comprising: a body having an aperture with a slot formed in said body extending radially from said aperture and further wherein a slidable member is positioned within said slot for abutment against said cutting edge of said atherotome, said slidable member being urged to press against said atherotome to collapse said balloon.

12. A method of manufacturing a folding balloon catheter as recited in claim further comprising positioning said cutting edge in said slot in abutment with said slidable member and performing said contracting step by sliding said member toward said aperture to displace said atherotome toward the longitudinal axis of said balloon.

13. A method of manufacturing a folding balloon catheter as recited in claim 12 wherein contact between said cutting edge and said member is cushioned by an elastomeric pad affixed to said member.

14. A method of manufacturing a folding balloon catheter as recited in claim 11 wherein said slidable member is biased toward said aperture.

15. A method of manufacturing a folding balloon catheter having a balloon with a wall enclosing an expandable chamber and a hollow catheter penetrating said chamber, the method comprising:
   applying a patch of a curable elastomeric material in an uncured state to the exterior of said wall while said chamber is in an expanded state;
   mounting an atherotome on said patch of uncured elastomeric material, wherein said atherotome has a cutting edge facing radially outward from the longitudinal axis of said balloon;
   partially curing said balloon by heating said balloon to a predetermined partial curing temperature and maintaining said partial curing temperature for a predetermined partial curing time;
   positioning said balloon in an aperture of a body, wherein said body has a slot formed therein extending radially away from said aperture such that said atherotome is positioned within said slot, and further wherein a member is slidably positioned within said slot in abutment with said cutting edge;
   sliding said member toward said aperture to displace said atherotome toward the longitudinal axis of said balloon, thereby forming a rounded furrow at said patch; and curing said balloon to completion by heating said material to a predetermined final curing temperature and maintaining said final curing temperature for a predetermined final curing time, thereby enabling repeated contraction of said chamber from said expanded state to said contracted state by folding said wall along said fold.

16. A method of manufacturing a folding balloon catheter as recited in claim 15 wherein said member is biased toward said aperture.

17. A method of manufacturing a folding balloon catheter as recited in claim 15 wherein a fluid is withdrawn from said chamber while sliding said member.

18. A method of manufacturing a folding balloon catheter having an elongated balloon enclosing an expandable chamber and a hollow catheter tube attached to the balloon in fluid communication with the chamber, the method comprising the steps of:

introducing fluid into said chamber to inflate said balloon;

applying at least one patch of an elastomeric material to the exterior of said balloon; partially curing said inflated balloon by heating said balloon to a predetermined partial curing temperature and maintaining said partial curing temperature for a predetermined partial curing time;

withdrawing fluid from said chamber to collapse said balloon at said patches to form rounded furrows thereat, so as to fold said balloon and create flaps between said patches; and curing said collapsed balloon by heating said material to a predetermined final curing temperature and maintaining said final curing temperature for a predetermined final curing time.

\* \* \* \* \*

UNITED STATES PATENT AND TRADEMARK OFFICE
CERTIFICATE OF CORRECTION

PATENT NO. : 5,209,799

DATED : May 11, 1993

INVENTOR(S) : Dennis Vigil

It is certified that error appears in the above-identified patent and that said Letters Patent is hereby corrected as shown below:

Column 8, line 32, after the word "claim" and before the word "further" insert --11--.

Signed and Sealed this

Thirteenth Day of December, 1994

Attest:

BRUCE LEHMAN

*Attesting Officer*     *Commissioner of Patents and Trademarks*